United States Patent [19]

Morse

[11] 4,185,993
[45] Jan. 29, 1980

[54] HERBICIDAL COMPOSITIONS AND METHODS

[75] Inventor: Max A. Morse, Streetsville, Canada

[73] Assignee: Ciba-Geigy AG, Basel, Switzerland

[21] Appl. No.: 415,559

[22] Filed: Nov. 14, 1973

[30] Foreign Application Priority Data

Nov. 14, 1972 [GB] United Kingdom ............... 52643/72

[51] Int. Cl.$^2$ ............................................. A01N 9/22
[52] U.S. Cl. ....................................................... 71/93
[58] Field of Search .............................................. 71/93

[56] References Cited

U.S. PATENT DOCUMENTS

| | | | |
|---|---|---|---|
| 2,891,855 | 6/1959 | Gysin et al. | 71/93 |
| 3,207,756 | 9/1965 | Knusli et al. | 71/93 X |
| 3,492,110 | 1/1970 | Hood et al. | |
| 3,634,062 | 1/1972 | Berrer | 71/93 X |

FOREIGN PATENT DOCUMENTS

| | | | |
|---|---|---|---|
| 1927010 | 1/1970 | Fed. Rep. of Germany | 71/93 |
| 7000419 | 7/1970 | Netherlands | 71/93 |

*Primary Examiner*—Catherine L. Mills
*Attorney, Agent, or Firm*—Wenderoth, Lind & Ponack

[57] ABSTRACT

Herbicidally active compositions having as the essentially active ingredients a mixture of prometryne, terbutryne, and at least one member selected from the group consisting of atrazine and simazine. There is also disclosed a method of controlling undesirable vegetation using these compositions.

16 Claims, No Drawings

HERBICIDAL COMPOSITIONS AND METHODS

This invention relates to herbicidal compositions.

More particularly, one aspect of this invention relates to herbicidal compositions having improved properties; in a further aspect of this invention, there is provided a method of treating undesired vegetation to obtain improved control over the vegetation.

There are a large number of known herbicidal compositions in use for controlling undesired vegetation. Still further, many times the number of herbicidal compositions in use have been proposed in the art for different uses, but, for one reason or another have not been accepted.

The herbicidal compositions employed are based on either a single active ingredient in which that active ingredient possesses a sufficient spectrum of activity to control either selective weed species or a broader spectrum comprising a combination of weed species, or in the alternative, such compositions contain two or more active ingredients designed to provide a broader spectrum control of weed species by the combined action or synergistic action, of the active ingredients. In most cases, the use of a herbicidal composition containing a single active ingredient is not normally sufficient to provide a broad spectrum control of weed species and hence, many compositions today are based on the combination of two or more active ingredients. The present invention deals particularly with the latter type of composition.

Again, in the prior art, many different combinations of active ingredients have been proposed. In general, the effect of these active ingredients can be either additive or cumulative on one hand, or on the other hand, it is synergistic. In either case, the result is the effect of a broader control of weed species than would normally be encountered by merely employing a single active ingredient in the composition.

As is well known in the art, many conventional herbicides that have been employed for many years are being discarded for several reasons, including the fact that they are no longer as effective as they originally were, or on the other hand, have been found to have undesirable side effects such as high residue values which do not permit the sowing of what is known in the art as "susceptible" crops in the soil the following year, etc. These disadvantages are such that even in the art today, a large amount of money is being spent on research and development for either new chemical compounds which do not have the disadvantageous properties of the prior art compositions or alternately, by attempting to develop new compositions containing different ingredients which exert an acceptable commercial control, but which do not have the disadvantages of the prior art compositions.

In the prior art, the compounds atrazine, simazine, prometryne and terbutryne are well known herbicidally active compounds which are extensively used for various purposes. In fact, heretofore, e.g. atrazine has been combined with other herbicidally active compounds to improve its weed spectrum—e.g. atrazine has been combined with terbutryne; terbutryne has been combined with simazine, etc. Individually or in such combinations, each of these active ingredients has several disadvantages known to those skilled in this art. For example, with respect to simazine, it is known that this active ingredient is less effective in controlling undesired vegetation in dry spells. Atrazine per se is well known and is an established herbicidally active ingredient; however, it is known from data that it is weak on crabgrass (regardless of rates) and in some cases, exhibits a weakness in controlling foxtail. In addition, atrazine like other similar herbicides, has a high residue level in soils and this and similar types of triazine herbicides have been shown to have a long residual life rendering it impossible for farmers to plant some susceptible crops in the same soil for at least the following year. Prometryne has the very disadvantageous characteristic that at rates required to exhibit at least marginally acceptable control of the undesired vegetation, it is quite phytotoxic to different types of crops including corn. In fact, the phytotoxicity of this product to corn is beyond the level of acceptability to farmers. In a like manner, terbutryne is also highly unsafe at higher dosage rates, e.g. 3–5 lbs. per acre to host crops such as corn and it can only control certain types of undesired vegetation.

With this invention, applicant has discovered a novel herbicidal composition which overcomes the disadvantages associated with the preceding type of compounds or compositions containing two of such active ingredients together, and which compositions of the present invention exhibit unexpected results based on the combination of such active ingredients. More particularly, in accordance with this invention, applicant has provided a herbicidal composition comprising as the active ingredients, a mixture of terbutryne, prometryne and at least one member of the group consisting of atrazine and simazine.

In accordance with a further aspect of this invention, applicant has discovered an improved method of controlling undesired vegetation which comprises the step of applying to the locus to be treated a herbicidally effective amount of a composition comprising as active ingredients, a mixture of terbutryne, prometryne and at least one member of the group consisting of atrazine and simazine.

For most applications, the active ingredients of the compositions of the present invention will be combined together with a carrier, and applied to the locus to be treated. Such carriers are well known by those skilled in this art and need not be enumerated in detail. However, as with conventional practices in this art, the carrier may be any inert dry or liquid carrier, with which the active ingredients may be intimately blended. In some cases, however, and depending on the intended use of the compositions of the present invention, such carriers may not be essential, as the active ingredients may be directly applied to the locus to be treated.

When using a carrier, and in the case of dry carriers, various types may be employed and typically, the solid diluent may be, e.g. clay, diatomaceous earth, synthetic carriers, etc. Such dry compositions may be blended as wettable powders and applied as sprays using water as vehicle, or if formulated without wetting agent, with suitable dust applying apparatus, or such compositions may be formulated in the form of granules or pellets.

The active ingredients may also be formulated as ready to use aqueous suspensions or oil dispersions with suitable wetting and emulsifying agents added thereto.

To prepare the compositions of the present invention, the active ingredients are normally blended together with the carrier in a suitable type of apparatus, again according to procedures well known to those skilled in this art. The blending of the active ingredients will take place in the proportion desired within the teachings of this invention; during blending or subsequent to it, various other additives well known to those skilled in this art may also be incorporated into the compositions—such additives being, e.g. stabilizers, emulsifiers, pH adjusting agents, chelating agents, wetting agents, dispersing agents, etc. These additional additives are normally incorporated in minor amounts into the compositions (e.g. in amounts of less than ½% by weight of the active ingredients).

The ratio of the terbutryne to the combined weight of the other active ingredients of the composition should be less than about 8:1 to about 1:9. The prometryne is preferably present in an amount of from about 3:1 to about 1:6, based on the weight of the atrazine and/or simazine.

In the compositions of the present invention, the most advantageous and effective results in which the compositions demonstrate their improved properties have been found when the terbutryne is present in an amount of from about 1:1 to about 1:7 of the combined weight of the prometryne and at least one of the group of atrazine and simazine, and in such case, when the prometryne is present in a weight proportion, based on active ingredients, of from about 2:1 to about 1:5 of the atrazine and/or simazine. As used in this specification, the weight ratios of one active ingredient to the other(s) are calculated on the basis of the actual weight ratio of the active ingredient.

As embraced by this invention, the third active ingredient of the compositions may either be atrazine or simazine or both. When employed in combination, i.e. when both atrazine and simazine are included in the compositions, the weight ratio of one to the other may vary within about 2:1 to about 1:2 calculated on the above basis of active ingredients.

If desired, additional active ingredients may be incorporated into the compositions of this invention in an additive manner. Thus, for example, other herbicides may also be included in the compositions of the present invention for certain purposes. However, their inclusion is optional and as will be evident from the teachings of the present invention, the compositions claimed in this applicable exhibit a wide spectrum of control over various weed species without the necessity of including further active ingredients.

In carrying out the method of the present invention, the above described compositions may be applied to the undesired vegetation. Applicant has found that the above compositions may be used according to the method of the present invention for excellent pre-emergent control of various weeds, such as would be encountered in various crops such as vegetable crops, e.g. corn, soya beans, sugar cane, etc. However, the compositions of the present invention may also be used to obtain excellent control over undesired vegetation as a pre- and/or post-emergent treatment to various types of host crops—and as well, for treating fallow land.

In carrying out the method of the present invention, and in the case of using the compositions as a pre-emergent herbicide, the compositions are applied at a total active ingredient concentration of from about 0.5 to about 5 lbs per acre, and desirably at a rate of from about 1 to about 4 lbs of total active ingredients per acre. However, it will be understood by those skilled in this art that such rates will vary, depending on the type of locus being treated, whether the compositions are used as pre- or post-emergence herbicides or for treating fallow land, as well as the type of soil being treated and other similar factors.

The compositions of the present invention may be applied by various methods to the locus to be treated, well known to those skilled in this art. To this end, the compositions may be sprayed or similarly applied to the soil surface; in the alternative, the compositions may be applied by dusting techniques or directly applied to the soil per se, particularly when in a dry form.

The compositions of the present invention provide many advantageous features over prior art proposals, and in particular, those which are commercially used for control of undesired vegetation in host crops such as corn, etc. For example, the compositions have been proven to provide effective commercial control of a broad spectrum of weed species, such as green foxtail, fall panicum, crabgrass, ragweed, yellow foxtail, mustard, red root pigweed, lady's thumb, lamb's quarters, wild buckwheat, old witchgrass, barnyard grass and the like.

Control of these weed species can be obtained at dosage rates of the active ingredients in the compositions of the present invention at levels below that which would normally be used for control of only a limited number of species by the individually active ingredients per se, or a combination of, e.g. two such active ingredients. The compositions of the present invention provide such control over the undesired vegetation at rates and control levels which would not be expected or predicted from the teachings of the prior art, as will be evidenced by the examples of this application. By virtue of the use of the compositions of the present invention, lower amounts of the active ingredients which have heretofore been employed for weed control in, e.g. various host crops, are hence utilized and this has resulted in lowering of the levels of soil residue of the chemicals which had a long residue life when applied at rates normally required to provide commercial control of undesired vegetation. Still further, and in addition to the above, the compositions of the present invention provide excellent weed control without injury to the host crop—a factor which has heretofore resulted in the use of lower amounts of active ingredients to avoid injury to the host crops, but at the same time, which resulted in marginal or inadequate control of the weed species. The unexpected safety factor of the compositions of the present invention thus permits the use of such active ingredients which can control undesired vegetation at higher rates while obtaining the same crop yields and other important economic benefits to the farmers.

Having thus generally described the invention, reference will now be made to the accompanying examples, illustrating preferred embodiments only.

EXAMPLE 1

The following compositions were prepared containing the active ingredients noted below.

| Composition | Active Ingredients |
|---|---|
| 1 | Atrazine |
| 2 | Atrazine and prometryne |
| 3 | Simazine |
| 4 | Terbutryne |
| 5 | Atrazine and terbutryne |
| 6 | Atrazine, terbutryne and prometryne |
| 7 | Simazine, terbutryne and prometryne |

The above compositions were formulated according to conventional practices well known to those skilled in this art, by blending together the active ingredients in the proportions hereinafter mentioned, together with a carrier. In compositions 2 and 5 the active ingredients were present in an amount of a 1:1 weight ratio basis, based on the weight of the active ingredients. In compositions 6 and 7 of the present invention, all active ingredients were present in a 1:1:1 weight ratio, calculated on the basis of the active ingredients.

The above compositions were prepared for spray application for use in various tests, as described in the subsequent examples.

EXAMPLE 2

The compositions of Example 1 were used as pre-emergent herbicidal compositions, as follows:

Cornseed was sown in replicated plots in a heavy clay loam type of soil. The corn plants had not yet sprouted. The weed infestation consisted primarily of green foxtail, with minor amounts of other weeds such as ragweed.

The above compositions 1 through 7 were applied to four replicate plots for each type of composition, at the rates outlined below. Specifically, randomized plots, generally of a twelve by twenty foot area, were chosen. Four such plots were used for each test for each composition.

Reading of the replicate plots for these examples was carried out approximately twelve weeks after the crop has been sown; the following Table provides the results of the average readings of the four replicate randomized plots for each composition used. The readings provided in the following Table are based on a scale of 1 to 9 (as defined by the European Weed Research Council), relative to the weeds, with 1 being the best control and 9 being no control. Under the conditions of assessment, a reading of 4.0 to 0 is considered commercially acceptable.

Table I

| Composition | Dosage Rate lb/acre (Active Ingredients) | Average Weed Control Rating |
| --- | --- | --- |
| 1 | 2.0 | 4.8 |
| 1 | 2.5 | 5.5 |
| 2 | 3.0 | 2.0 |
| 3 | 2.5 | 1.9 |
| 4 | 2.5 | 5.3 |
| 5 | 2.5 | 2.0 |
| 6 | 2.0 | 1.3 |
| 7 | 2.0 | 1.5 |
| Check | — | 8.5 |

From the above data in Table I, it will be seen first of all that the treatments using atrazine as the sole active ingredient, and terbutryne as the sole active ingredient, failed to provide acceptable commercial control. Commercial control is achieved by using 3 lbs of a mixture of atrazine and prometryne; composition 6, on the other hand, provided a weed control rating of 1.3 or slightly better than the weed control rating of composition 2 but using 1 lb less per acre or 33% less of total active ingredient as compared to composition 2, clearly demonstrating the synergistic effect of this three-way composition. In a similar vein, 25% less total active ingredient of composition 6 yielded slightly better weed control than composition 5. Still further, the improved results of composition 7 will be evident from the above Table in which 2 lbs of total active ingredient of composition 7 gave better weed control using 25 to 33% less total active ingredient than a single or two-way composition treatment.

It is significant to point out that the unexpected advantage that the compositions yield in terms of improved results is coupled with the fact that when using the compositions of the present invention, the residue amounts remaining in the soil after applying the lesser amounts of the individual components of the compositions of the present invention are low enough to permit farmers to plant normally susceptible crops the following year without danger to the crops—which would not be the case with the use of compositions containing atrazine or simazine in the dosages indicated for compositions, e.g. numbers 1 and 3.

EXAMPLE 3

This Example again demonstrates the results obtained by using the above described compositions, as pre-emergent herbicides, in a corn field of a sandy loam type soil.

Table II

| Composition | Dosage Rate lb/acre (Active Ingredients) | Average Weed Control Rating |
| --- | --- | --- |
| 1 | 2.0 | 6.0 |
| 1 | 2.5 | 5.8 |
| 2 | 3.0 | 4.3 |
| 3 | 2.5 | 2.4 |
| 4 | 2.5 | 4.3 |
| 5 | 2.5 | 4.8 |
| 6 | 2.0 | 3.5 |
| 7 | 2.0 | 2.1 |
| 7 | 3.0 | 1.4 |
| Check | — | 8.5 |

The weed species present in the unsprayed check plot were ragweed and green foxtail. Wherever these two weeds were eliminated, crabgrass became the dominant species. The ratings, therefore, of Table II are based on crabgrass control.

From the above Table, it will be seen that the combination of atrazine plus prometryne, even at dosage rates of 3 lbs total active ingredients per acre, and atrazine by itself even at dosage rates of 2.5 lbs of active ingredient per acre, failed to yield acceptable control. Similarly terbutryne and a combination of atrazine and terbutryne still did not yield acceptable control at dosage rates of 2.5 lbs of active ingredient per acre. The only composition at the relatively high dosage rate of 2.5 lbs of active ingredient per acre, which yielded acceptable control was simazine, with the rating of 2.4.

Simazine, composition 3, is a good crabgrass control herbicide by itself as is indicated by this satisfactory rating. Surprisingly, a reduction of the simazine rate per acre by 74% when combined with two active ingredients relatively ineffective against crabgrass, composition 7, gave superior crabgrass control to simazine using 25% less total active ingredients than simazine alone.

Composition 1, atrazine alone or combined with prometryne (composition 2), or combined with terbutryne, (composition 5), gives unsatisfactory control of crabgrass. The three-way mixture of these ingredients, composition 6, at a minimum rate of 2 lbs total active ingredient gave commercially acceptable control.

EXAMPLE 4

Using the compositions of Example 1, and by following the procedures described previously, the compositions of Example 1 were utilized as pre-emergent herbicides in a corn field, in which the weed population included a majority of crabgrass with lesser amounts of ragweed, and Chenopodium album. The test conditions for this example were severe due to weather conditions; the following results were obtained for weed control for the various compositions.

Table III

| Composition | Dosage Rate lb/acre (Active Ingredients) | Average Weed Control Rating |
|---|---|---|
| 2 | 3.0 | 6.3 |
| 3 | 2.5 | 6.9 |
| 4 | 2.5 | 5.5 |
| 7 | 2.0 | 2.8 |
| Check | — | 9.0 |

From the above table, it will be seen that the compositions of the present invention, composition 7, yielded satisfactory control whereas the individual active ingredients, simazine and terbutryne, failed to provide any acceptable control.

EXAMPLE 5

This example is a summary of replicated tests using the compositions of Example 1 and by following the procedures of Example 2. Again, the herbicidal compositions were used as pre-emergent treatments for a field crop, and in this test, the primary weed infestation was with crabgrass with minor amounts of green foxtail; the weed infestation comprises a major amount of green foxtail with a minor amount of ragweed. The results are shown in separate columns in Table IV.

Table IV

| Composition | Dosage Rate lb/acre (Active Ingredients) | Average Weed Control Rating |
|---|---|---|
| 1 | 2.0 | 6.5 |
| 1 | 2.5 | 8.5 |
| 2 | 3.0 | 3.3 |
| 3 | 2.5 | 5.9 |
| 4 | 2.5 | 2.9 |
| 5 | 2.5 | 5.8 |
| 6 | 2.0 | 3.3 |
| 7 | 2.0 | 2.3 |
| Check | — | 9.0 |

From the above data it will be seen that composition 6 and composition 7 at the 2 lb dosage rate give weed control ratings of 3.3 and 2.3 respectively which is 25% to 33% less total active ingredients than any of the other compositions except composition 1 which gave very inferior results in terms of weed control. Compositions 2 and 4 gave commercial control but the dosage rates were substantially higher at 3 lb and 2.5 lb active ingredient respectively.

The conversion of the data on each of the above experiments together with others similarly carried out, yielded an overall average for each composition for comparison of broad spectrum weed control as follows:

Table V

| Composition | Dosage Rate lb/acre (Active Ingredients) | Average Weed Control Rating |
|---|---|---|
| 1 | 2.0 | 4.5 |
| 1 | 2.5 | 4.3 |
| 2 | 3.0 | 2.8 |
| 3 | 2.5 | 2.8 |
| 4 | 2.5 | 4.1 |
| 5 | 2.5 | 3.2 |
| 6 | 2.0 | 2.9 |
| 7 | 2.0 | 1.8 |

Table V-continued

| Composition | Dosage Rate lb/acre (Active Ingredients) | Average Weed Control Rating |
|---|---|---|
| Check | — | 8.0 |
| 8 | 1 + 2 | 3.0 |
| 9 | 1 + 2 | |

Composition 8 was composed of atrazine and the product marketed under the common name "ALACHLOR".

Composition 9 was composed of atrazine and the product marketed under the common name "CYANAZINE".

From the above summary, it will be seen that overall, atrazine by itself failed to provide acceptable commercial weed control at dosages of 2.0 and 2.5 lbs of active ingredients per acre; likewise, terbutryne failed to achieve acceptable control at dosage rates of 2.5 lbs of active ingredient. Composition 6 of the present invention, at 2.0 lbs provided acceptable commercial control at a rating substantially the same as that of 3 lbs of the mixture of atrazine and prometryne and 2.5 lbs of the mixture of atrazine and terbutryne, yet using only 2 lbs of total active ingredients. Simazine, composition 3, under adequate moisture conditions performs well but under dry conditions it may perform very inadequately. In this case, it gives satisfactory control but at a dosage rate 25% greater than that of compositions 6 and 7.

EXAMPLE 6

The compositions noted below were prepared using the active ingredients and the weight ratios (calculated on the amounts of active ingredient) indicated.

| Composition | Active Ingredient(s) and Weight Ratio(s) | | |
|---|---|---|---|
| 10 | Terbutryne: | (Simazine + Prometryne) | = 1:1.5 |
| | | Simazine : Prometryne | = 1:2 |
| 11 | Terbutryne: | (Simazine + Prometryne) | = 1:2 |
| | | Simazine : Prometryne | = 1:1 |
| 12 | Terbutryne: | (Simazine + Prometryne) | = 1:3 |
| | | Simazine : Prometryne | = 2:1 |
| 13 | Terbutryne: | (Simazine + Prometryne) | = 1:4 |
| | | simazine : Prometryne | = 3:1 |
| 14 | Terbutryne: | (Simazine + Prometryne) | = 1:5 |
| | | Simazine : Prometryne | = 4:1 |
| 15 | Terbutryne: | (Simazine + Prometryne) | = 1:6 |
| | | Simazine : Prometryne | = 5:1 |
| 16 | Terbutryne: | (Atrazine + Prometryne) | = 1:2 |
| | | Atrazine : Prometryne | = 1:1 |
| 17 | Terbutryne: | (Atrazine + Prometryne) | = 1:3 |
| | | Atrazine : Prometryne | = 2:1 |
| 18 | Terbutryne: | (Atrazine + Prometryne) | = 1:4 |
| | | Atrazine : Prometryne | = 3:1 |
| 19 | Terbutryne: | (Atrazine + Prometryne) | = 1:5 |
| | | Atrazine : Prometryne | = 4:1 |
| 20 | Terbutryne: | (Atrazine + Prometryne) | = 1:6 |
| | | Atrazine : Prometryne | = 5:1 |
| 21 | Terbutryne | | — |
| 22 | Atrazine | | — |
| 23 | Prometryne | | — |
| 24 | Simazine | | — |
| 25 | Terbutryne + Prometryne | | = 9:1 |
| 26 | Terbutryne + Atrazine | | = 9:1 |
| 27 | Terbutryne + Simazine | | = 8.5:1 |
| 28 | Atrazine + Prometryne | | = 13:1 |

The above compositions were formulated according to conventional practices and techniques well known to those skilled in this art. To this end, where there were two or more active ingredients, the active ingredients were blended together in the weight ratio proportions given above. All compositions were blended with a carrier. The above compositions thus prepared, were utilized for the following examples as described hereinafter.

EXAMPLE 7

This example is a report of tests carried out using compositions 10 through 28 described above, to determine the effectiveness of the compositions as herbicidally active agents for the control of undesired vegetation.

These tests were carried out by treating replicated plots in a very cloddy soil, in which the predominant weed species was green foxtail, with minor amounts of the following weed species: Ragweed, Smartweed, Wild Buckwheat, Barnyardgrass, Red Root Pigweed and Hairy Crabgrass.

Prior to treatment, the land was divided into replicated plots and each of compositions 10–28 was applied to three randomized plots throughout the test area. These compositions were applied to the plots using a plot sprayer following planting of a vegetable crop (corn) in early summer. The application rate of each composition is as shown in the following table.

Assessment of the replicate plots for weed control was carried out at three different spaced intervals during the summer, to determine the weed control exhibited by the respective compositions. The readings of the weed control, as summarized in the following table, are based on a scale of 1 to 9 (as defined by the European Weed Research Council) relative to the weeds, with 1 being the best control and 9 representing no control. Under the conditions of assessment, a reading of 4.0 to 0 is considered commercially acceptable.

Table VI

| Composition | Dosage Rate lb/acre (Active Ingredients) | Average Weed Control Rating |
| --- | --- | --- |
| 10 | 2.5 | 3.3 |
|    | 3.0 | 3.0 |
| 11 | 2.0 | 3.7 |
|    | 3.0 | 2.8 |
| 12 | 2.0 | 2.7 |
|    | 3.0 | 1.3 |
| 13 | 2.5 | 1.5 |
|    | 3.0 | 2.3 |
| 14 | 2.5 | 2.3 |
|    | 3.0 | 1.8 |
| 15 | 2.5 | 1.8 |
|    | 3.0 | 1.7 |
| 16 | 3.0 | 3.7 |
| 17 | 2.5 | 3.7 |
| 18 | 2.5 | 3.5 |
| 19 | 3.0 | 3.5 |
| 20 | 2.5 | 3.7 |
| 21 | 2.8 | 4.8 |
|    | .2  | 7.7 |
|    | 1.5 | 5.0 |
| 22 | .02 | 7.0 |
|    | 1.5 | 5.7 |
|    | 3.0 | 4.5 |
| 23 | .2  | 7.7 |
|    | .675 | 7.0 |
|    | 1.5 | 4.8 |
|    | 3.0 | 2.5 |
| 24 | 2.4 | 4.7 |
|    | 1.5 | 4.2 |
|    | 3.0 | 1.8 |
| 25 | 1.49 | 5.7 |
| 26 | 1.47 | 6.2 |
| 27 | 1.46 | 6.2 |
| 28 | 1.41 | 6.2 |
| Check | — | 8.8 |

From the above data it will be seen that the compositions of the present invention all yielded acceptable commercial control and more surprisingly, compared to the compositions containing the individual active ingredients, in the compositions of the present invention, superior control was generally obtained using lower dosage rates. In this trial the commercially used herbicides prometryne and simazine also gave good weed control at the high rate of 3 lbs per acre. It must be explained here, however, that prometryne at 3 lbs per acre is not tolerated by corn and causes serious injury and reduction of yield. Also simazine at 3 lbs per acre causes an undesirable soil residue harmful to sensitive crops planted the following year, whereas the advantage of the compositions of this invention is that good weed control is provided during the season of the application but without any undesirable residue.

As used herein, the common names for certain chemicals have the following meaning: atrazine is 2-chloro-4-ethylamino-6-isopropylamino-S-triazine; simazine is 2-chloro-4,6-bis(ethylamino)-S-triazine; prometryne is 2,4-bis(isopropylamino)-6-methylthio-S-triazine; and terbutryne is 2-tert.-butylamino-4-ethylamino-6-methylthio-S-triazine.

I claim:

1. A herbicidal composition suitable for achieving pre-emergent herbicidal activity in corn crops, comprising a herbicidally effective amount of a mixture of active ingredients consisting essentially of 2,4-bis(isopropylamino)-6-methylthio-S-triazine, 2-tert-butylamino-4-ethylamino-6-methylthio-S-triazine and at least one member selected from the group consisting of 2-chloro-4-ethylamino-6-isopropylamino-S-triazine and 2-chloro-4,6-bis(ethylamino)-S-triazine, said triazines being the only active ingredients in the composition, the weight ratio of 2-tert-butylamino-4-ethylamino-6-methylthio-S-triazine to the combined weight of the other active ingredients in the mixture being from about 8:1 to about 1:9 and the weight ratio of 2,4-bis(isopropylamino)-6-methylthio-S-triazine to 2-chloro-4-ethylamino-6-isopropylamino-S-triazine, 2-chloro-4,6-bis(ethylamino)-S-triazine or mixture thereof being from about 3:1 to about 1:6.

2. A composition as defined in claim 1, wherein the active ingredients are 2,4-bis(isopropylamino)-6-methylthio-S-triazine, 2-tert-butylamino-4-ethylamino-6-methylthio-S-triazine and 2-chloro-4-ethylamino-6-isopropylamino-S-triazine.

3. A composition as defined in claim 1, wherein the active ingredients are 2,4-bis(isopropylamino)-6-methylthio-S-triazine, 2-tert-butylamino-4-ethylamino-6-methylthio-S-triazine, 2-chloro-4-ethylamino-6-isopropylamino-S-triazine and 2-chloro-4,6-bis(ethylamino)-S-triazine.

4. A composition as defined in claim 1, wherein the active ingredients are 2,4-bis(isopropylamino)-6-methylthio-S-triazine, 2-tert-butylamino-4-ethylamino-6-methylthio-S-triazine and 2-chloro-4,6-bis(ethylamino)-S-triazine.

5. A composition as defined in claim 1, wherein the weight ratio of 2-tert-butylamino-4-ethylamino-6-methylthio-S-triazine to the combined weight of the other active ingredients in the mixture is from 1:1 to about 1:7.

6. A composition as defined in claim 3, wherein the weight ratio of 2-tert-butylamino-4-ethylamino-6-methylthio-S-triazine to the combined weight of the other active ingredients in the mixture is from about 1:1 to about 1:7.

7. A composition as defined in claim 1, wherein the weight ratio of 2,4-bis(isopropylamino)-6-methylthio-S-triazine to 2-chloro-4-ethylamino-6-isopropylamino-S-triazine, 2-chloro-4,6-bis(ethylamino)-S-triazine or mixture thereof is from about 2:1 to about 1:5.

8. A composition as defined in claim 3, wherein the weight ratio of 2,4-bis(ispropylamino)-6-methylthio-S-triazine to the combined weight of 2-chloro-4-ethylamino-6-isopropylamino-S-triazine and 2-chloro-4,6-bis(ethylamino)-S-triazine is from about 2:1 to about 1:5.

9. A composition as defined in claim 1, wherein said composition contains a carrier for the mixture of active ingredients.

10. A composition as defined in claim 3, wherein said composition contains a carrier for the mixture of active ingredients.

11. A method for achieving pre-emergent herbicidal activity in corn crops, thus controlling undesired vegetation, which comprises applying to the locus to be treated a herbicidally effective amount of a composition comprising a mixture of active ingredients consisting essentially of 2,4-bis(isopropylamino)-6-methylthio-S-triazine, 2-tert-butylamino-4-ethylamino-6-methylthio-S-triazine and at least one member selected from the group consisting of 2-chloro-4-ethylamino-6-isopropylamino-S-triazine and 2-chloro-4,6-bis(ethylamino)-S-triazine, said triazines being the only active ingredients in the composition, the weight ratio of 2-tert-butylamino-4-ethylamino-6-methylthio-S-triazine to the combined weight of the other active ingredients in the mixture being from about 8:1 to about 1:9 and the weight ratio of 2,4-bis(isopropylamino)-6-methylthio-S-triazine to 2-chloro-4-ethylamino-6-isopropylamino-S-triazine, 2-chloro-4,6-bis(ethylamino)-S-triazine or mixture thereof being from about 3:1 to about 1:6.

12. A method as defined in claim 11, wherein said composition is applied to said locus together with a carrier for the mixture of active ingredients.

13. A method as defined in claim 11, wherein the weight ratio of 2-tert-butylamino-4-ethylamino-6-methylthio-S-triazine to the combined weight of the other active ingredients in the mixture of the composition is from about 1:1 to about 1:7 and the weight ratio of 2,4-bis(isopropylamino)-6-methylthio-S-triazine to 2-chloro-4-ethylamino-6-isopropylamino-S-triazine, 2-chloro-4,6-bis(ethylamino)-S-triazine or mixture thereof in the composition is from about 2:1 to 1:5.

14. A method as defined in claim 11, wherein the active ingredients in the composition are 2,4-bis(isopropylamino)-6-methylthio-S-triazine, 2-tert-butylamino-4-ethylamino-6-methylthio-S-triazine and 2-chloro-4,6-bis(ethylamino)-S-triazine.

15. A method as defined in claim 11, wherein said composition is applied at a total dosage rate of from about 0.5 to about 5.0 pounds per acre.

16. A method for achieving pre-emergent herbicidal activity in corn crops, thus controlling undesired vegetation, which comprises applying to the locus to be treated a herbicidally effective amount of a composition comprising a mixture of active ingredients consisting essentially of 2,4-bis(isopropylamino)-6-methylthio-S-triazine, 2-tert-butylamino-4-ethylamino-6-methylthio-S-triazine and 2-chloro-4-ethylamino-6-isopropylamino-S-triazine, said triazines being the only active ingredients in the composition, the weight ratio of 2-tert-butylamino-4-ethylamino-6-methylthio-S-triazine to the combined weight of the other active ingredients in the mixture being from about 8:1 to about 1:9 and the weight ratio of 2,4-bis(isopropylamino)-6-methylthio-S-triazine to 2-chloro-4-ethylamino-6-isopropylamino-S-triazine being from about 3:1 to about 1:6.

* * * * *